United States Patent [19]

Weaver et al.

[11] Patent Number: 4,749,773
[45] Date of Patent: Jun. 7, 1988

[54] CONDENSATION POLYMERS CONTAINING METHINE ULTRAVIOLET RADIATION-ABSORBING RESIDUES AND SHAPED ARTICLES PRODUCED THEREFROM

[75] Inventors: Max A. Weaver; Wayne P. Pruett, both of Kingsport; Samuel D. Hilbert, Jonesborough; Clarence A. Coates, Jr., Kingsport, all of Tenn.

[73] Assignee: Eastman Kodak Company, Rochester, N.Y.

[21] Appl. No.: 78,433

[22] Filed: Jul. 27, 1987

[51] Int. Cl.$^4$ .................... C08G 63/44; C08G 63/76; C08G 69/44

[52] U.S. Cl. .................... 528/288; 525/46; 525/445; 528/183; 528/192; 528/193; 528/194; 528/290; 528/302; 528/303; 528/304

[58] Field of Search ............ 528/288, 290, 302, 303, 528/304, 183, 192–194; 525/445, 46

[56] References Cited

U.S. PATENT DOCUMENTS 3,597,434  8/1971  Weaver ............................ 546/165
4,297,502 10/1981  Herrmann et al. ............ 528/288 X
4,617,373 10/1986  Pruett et al. ..................... 528/288

Primary Examiner—Lucille M. Phynes
Attorney, Agent, or Firm—J. Frederick Thomsen; William P. Heath, Jr.

[57] ABSTRACT

A composition useful for molding into articles such as food containers, soft drink bottles, cured structural plastics and the like, comprising molding grade linear or unsaturated polyester or polycarbonate having reacted or copolymerized therein a total of from 100 to about 800 ppm, of the residue of one or a mixture of methine reactants of the formula

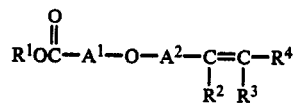

wherein $R^1$ is hydrogen or an unsubstituted or substituted alkyl, alkenyl, cycloalkyl or aryl radical;

$A^1$ is an unsubstituted or substituted phenylene radical;

$A^2$ is an unsubstituted or substituted 1,4-phenylene radical;

$R^2$ is hydrogen or an unsubstituted or substituted alkyl, cycloalkyl or aryl radical;

$R^3$ is cyano or

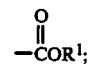

and $R^4$ is one of the substituents which $R^3$ can represent or an unsubstituted or substituted carbamoyl, alkanoyl, aroyl, alkylsulfonyl, arylsulfonyl, aryl or aromatic heterocyclic radicals.

The methine residues are present in the polymer as an integral part of the polymer chain and absorb ultraviolet radiation in the range of about 250 to about 390 nm. The residues are non-extractable from the polymer and stable at the conditions at which the polymers are manufactured and processed.

14 Claims, No Drawings

CONDENSATION POLYMERS CONTAINING METHINE ULTRAVIOLET RADIATION-ABSORBING RESIDUES AND SHAPED ARTICLES PRODUCED THEREFROM

DESCRIPTION

This invention pertains to novel condensation polymers such as polyesters and polycarbonates wherein an ultraviolet light screening amount of one or more methine moieties has been incorporated in the chain or backbone of the polymer. This invention also pertains to containers, such as those suitable for packaging beverages and foods, manufactured from our novel condensation polymers.

Many products such as certain fruit juices, soft drinks, wines, food products, cosmetics and shampoos are deleteriously affected, i.e., degraded, by ultraviolet (UV) light when packaged in plastic containers which pass significant portions of the available light at wavelengths in the range of approximately 250 to 390 nm. It is well known that polymers can be rendered resistant to degradation by UV light by physically blending in such polymers various UV light stabilizers such as benzophenones, benzotriazoles and resorcinol monobenzoates. See, for example, Plastics Additives Handbook, Hanser Publishers, Library of Congress, Catalog No. 83-062289, pp 128-134. Normally, such stabilizers are used in a weight concentration of at least 0.5 percent. Although these stabilizers function well to absorb radiation in the range of about 300 to 350 nm, absorbence in the range of 300 to 350 nm is not adequate to protect comestibles subject to UV light degradation packaged in clear plastic, i.e., essentially colorless, transparent plastic. The stabilizers in the known stabilized polymer compositions can be extracted from the polymer by solvents such as acids, alcohols and the like present in foods or beverages packaged within the stabilized polymers. Furthermore, many compounds used to stabilize polymers are not stable at high temperatures and would decompose under the conditions at which polyesters are manufactured or processed. Decomposition of such stabilizers frequently causes yellow discoloration of the polyester and results in the polyester containing little, if any, of the stabilizer.

U.S. Pat. No. 4,340,718 discloses the copolymerization of certain methine stabilizers with polyesters. The patent further discloses that the concentration of the methine stabilizers in the polyesters should be in the range of 0.3 to 5.0 percent, preferably 0.6 to 2.0 percent, i.e., 6000 to 20,000 ppm, to impart to the basic polyester improved weatherability in outdoor applications. This patent does not mention the use of methine compounds in low concentrations for the purpose of screening UV light.

U.S. Pat. No. 4,617,374 discloses that polyesters having certain methine compounds reacted therein to absorb light in the range of 320 to 380 nm. That patent, however, does not disclose the methine compounds used in the polyester compositions and articles molded therefrom provided by our invention.

Our invention concerns a composition comprising molding grade condensation polymer having copolymerized therein a total of about 100 to 800 parts by weight per million parts by weight polymer (ppm) of the residue of a methine compound or mixture of methine compounds having the formula

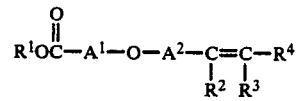

wherein $R^1$ is hydrogen or an unsubstituted or substituted alkyl, alkenyl, cycloalkyl or aryl radical;

$A^1$ is an unsubstituted or substituted phenylene radical;

$A^2$ is an unsubstituted or substituted 1,4-phenylene radical;

$R^2$ is hydrogen or an unsubstituted or substituted alkyl, cycloalkyl or aryl radical;

$R^3$ is cyano or

and $R^4$ is one of the substituents which $R^3$ can represent or an unsubstituted or substituted carbamoyl, alkanoyl, aroyl, alkylsulfonyl, arylsulfonyl, aryl or aromatic heterocyclic radicals.

Examples of the unsubstituted alkyl groups include methyl, ethyl, propyl, 2-propyl, butyl, 2-butyl, hexyl, octyl, 2-ethylhexyl, decyl, dodecyl, etc. The cycloalkyl groups may be cyclopentyl, cyclohexyl, cycloheptyl and the like. The aryl groups may be, for example, carbocyclic aryl such as phenyl and naphthyl. Examples of the unsubstituted alkanoyl, alkylsulfonyl and arylsulfonyl include acetyl, propionyl, butyryl, pivaloyl, hexanoyl, 2-ethylhexanoyl, methylsulfonyl, ethylsulfonyl, propylsulfonyl, octylsulfonyl, phenylsulfonyl, etc. Pyrolyl, pyridyl, pyrimidyl, 2-benzothiazolyl, 2-benzoxazolyl, 2-benzimidazoyl, 2-thienyl, 2-furanyl, 1,3,4-thiadiazol-2-yl, 1,2,4-thiadiazol-5-yl and groups having the structure

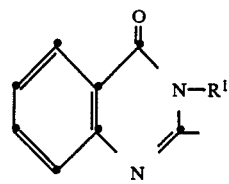

are examples of the unsubstituted aromatic heterocyclic residues which may constitute a part of the methine compounds. The alkyl radicals represented by $R^1$ and $R^2$ can be substituted with a wide variety of substituents such as alkoxy, alkylthio, halogen, hydroxy, cycloalkyl, cycloalkoxy, alkanoyloxy, cyano, aryl, aryloxy, arylthio, etc. The cycloalkyl, aryl and aromatic heterocyclic groups can be substituted with unsubstituted or substituted alkyl as well as with any of the substituents set forth hereinabove. Normally, those substituents containing alkyl moieties, such as alkyl, hydroxyalkyl, alkoxyalkyl, etc., will not contain more than a total of 12 carbon atoms. The unsubstituted and substituted cycloalkyl groups typically will contain from 5 to 12 carbon atoms whereas the unsubstituted and substituted aryl groups will contain from 6 to 12 carbon atoms. Illustrative of the phenylene radicals represented by $A^1$ and $A^2$ are groups having the structure

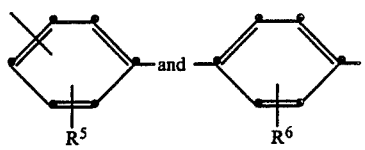 and 

respectively, wherein $R^5$ and $R^6$ are hydrogen, alkyl, alkoxy, halogen or $$-\overset{O}{\underset{}{\overset{\|}{C}}}OR^1.$$

The methine compounds which are particularly preferred have the formula

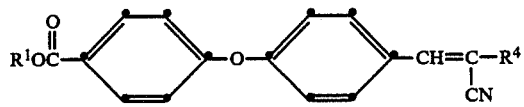

wherein $R^1$ is hydrogen or lower alkyl and $R^4$ is cyano, lower alkoxycarbonyl, carbamoyl, lower alkylsulfonyl, phenylsulfonyl, tolylsulfonyl, phenyl or tolyl, in which lower designates a carbon content of up to about 4 carbon atoms.

The methine compounds can be prepared using known procedures by reacting an intermediate carbonyl compound II with an active methylene compound III under Knovenagel reaction conditions, e.g.,

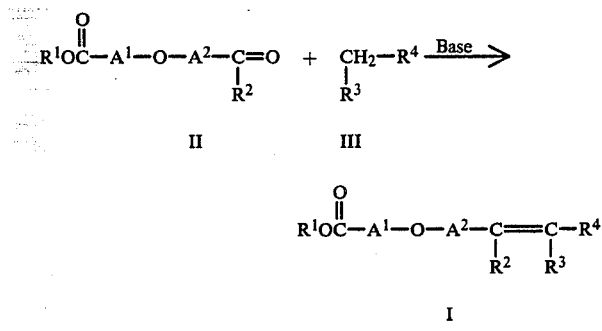

Lower alcohols such as methanol, ethanol and 2-propanol are usually suitable solvents. With certain reactants, for example when $R^3$ is not hydrogen, it is sometimes advantageous to conduct the reaction in a hydrocarbon solvent such as benzene or toluene to permit the water to be azeotropically removed as it is formed. Bases such as piperidine, piperidine acetate, pyrrolidine, sodium acetate and pyridine are effective in promoting the reaction.

Intermediate carbonyl compounds II wherein $R^2$ is hydrogen may be prepared according to the general procedure described in U.S. Pat. No. 2,754,286. Compounds II also may be obtained by reacting intermediate halogen compounds IV under Ullman reaction conditions with intermediate hydroxy compounds V:

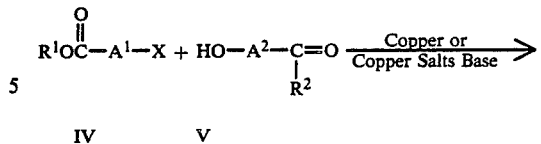

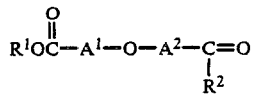

wherein X is halogen.

The polyesters which may be used in the preparation of the compositions of our invention include linear, thermoplastic, crystalline or amorphous polyesters produced by conventional polymerization techniques from one or more diols and one or more dicarboxylic acids. The polyesters normally are molding or fiber grade and have an inherent viscosity (IV) of about 0.4 to about 1.2. The preferred polyesters comprise at least about 50 mole percent terephthalic acid residues and at least about 50 mole percent ethylene glycol and/or 1,4-cyclohexanedimethanol residues. Particularly preferred polyesters are those containing from about 75 to 100 mole percent terephthalic acid residues and from about 75 to 100 mole percent ethylene glycol residues.

The unsaturated, curable polyesters which may be used in our novel compositions are the polyesterification products of one or more glycols and one or more unsaturated dicarboxylic acids or their anhydrides. Typical of the unsaturated polyesters is the polyesterification product of (a) 1,4-cyclohexanedimethanol and/or 2,2-dimethyl-1,3-propanediol and optionally an additional dihydric alcohol, such as ethylene glycol, and (b) maleic acid or fumaric acid and an aromatic dicarboxylic acid, which when crosslinked with an ethylenically-unsaturated monomer, e.g., styrene, produces a cured polyester resin which has, for example, high thermal resistance, high heat distortion values, excellent electrical and mechanical properties, and excellent resistance to chemicals.

Solutions of such unsaturated polyester resins in an ethylenically-unsaturated monomer such as styrene commonly are referred to as polyester resins.

The unsaturated polyester resins may be prepared in the presence of gelation inhibitors such as hydroquinone or the like, which are well known in the art of polyesterification. The esterification may be carried out for example under an inert blanket of gas such as nitrogen in a temperature range of 118°–220° C. for a period of about 6–20 hours until an acid number below 100 and preferably below 50 is obtained, based on milliequivalents of KOH necessary to neutralize 1 gram of the unsaturated polyester. The resulting polyester may be subsequently copolymerized, crosslinked, or cured with "curing amounts" of any of the well-known ethylenically unsaturated monomers used as solvents for the polyester. Examples of such monomers include styrene, alpha-methyl styrene, vinyl toluene, divinyl benzene, chlorostyrene, and the like as well as mixtures thereof. Typically, the mole ratio of such unsaturated monomer to the unsaturated moiety (e.g., maleic acid residue) in the polyester is from about 0.5 to about 3.0, although the "curing amounts" of such monomer can be varied from these ratios.

It is preferred that the unsaturated polyester be prepared from one or more dihydric alcohols, fumaric or maleic acid or mixtures thereof, and up to about 60 mole percent of total acid component of o-phthalic, isophthalic or terephthalic acids or mixtures thereof. Preferred for the dihydric alcohol component is one or a mixture of propylene glycol, neopentyl glycol, 2,2,4-trimethyl-1,3-pentanediol, ethylene glycol, or diethylene glycol. A specific preferred unsaturated polyester is prepared from about 75 to 100 mole percent propylene glycol, and as the acid component, from, about 75 to 100 mole percent o-phthalic and maleic acids in a mole ratio of from about 1/2 to about 2/1. Typical of these unsaturated polyesters are those disclosed, for example, in U.S. Pat. No. 4,359,570 incorporated herein by reference.

The diol components of the described polyesters may be selected from ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, 1,3-cyclohexanedimethanol, X,8-bis(hydroxymethyl)-tricyclo-[5.2.1.0]-decane wherein X represents 3, 4, or 5; and diols containing one or more oxygen atoms in the chain, e.g., diethylene glycol, triethylene glycol, dipropylene glycol, tripropylene glycol and the like. In general, these diols contain 2 to 18, preferably 2 to 8 carbon atoms. Cycloaliphatic diols can be employed in their cis or trans configuration or as mixtures of both forms.

The acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalene-dicarboxylic acid and the like. In the polymer preparation, it is often preferable to use a functional acid derivative thereof such as the dimethyl, diethyl, or dipropyl ester of the dicarboxylic acid. The anhydrides or acid halides of these acids may be employed where practical.

Typical polycarbonates useful herein are disclosed in Kirk-Othmer Encyclopedia of Chemical Technology, third edition, Volume 18, pages 479-494, incorporated herein by reference.

The novel polymer compositions provided by this invention are useful in the manufacture of containers or packages for comestibles such as beverages and food. By the use of known heat-setting techniques, certain of the polyesters are, in terms of color, I.V. and heat distortion, stable at temperatures up to about 100° C. Such stability characteristics are referred to herein as "hot-fill" stability. Articles molded from these polyesters exhibit good thin-wall rigidity, excellent clarity and good barrier properties with respect to moisture and atmospheric gases, particularly carbon dioxide and oxygen.

The linear polyesters most preferred for use in articles having "hot-fill" stability comprise poly(ethylene terephthalate) and poly(ethylene terephthalate) wherein up to 5 mole percent of the ethylene glycol residues have been replaced with residues derived from 1,4-cyclohexanedimethanol, wherein the polyesters have been sufficiently heat set and oriented by methods well known in the art to give a desired degree of crystallinity. By definition, a polymer is "hot-fill" stable at a prescribed temperature when less than 2% change in volume of a container manufactured therefrom occurs upon filling the same with a liquid at the temperature. For the manufacture of blow-molded beverage bottles, the most preferred polyesters have an I.V. of 0.65 to 0.85, and a Tg of >70° C., and film sections cut from the bottle have a Water Vapor Transmission Rate of 1.5 to 2.5 g. mils/100 in.$^2$-24 hrs., a Carbon Dioxide Permeability of 20-30 cc. mils/100 in.$^2$-24 hrs.-atm., and an Oxygen Permeability of 4-8 cc. mils/100 in.$^2$-24 hrs.-atm. The Tg is determined by Differential Scanning Calorimetry at a scan rate of 20 Centigrade Degrees/min., the Oxygen Permeability by the standard operating procedure of a MOCON OXTRAN 100 instrument of Modern Controls, Inc., of Elk River, Minn., and the Carbon Dioxide Permeability by the standard operating procedure of a MOCON PERMATRAN C II, also of Modern Controls.

The preparation of the methine compounds and their use in preparing the compositions of our invention are further illustrated by the following examples.

EXAMPLE 1

A mixture of 4-(4-methoxycarbonylphenoxy)benzaldehyde (2.56 g, 0.01 mol), methyl cyanoacetate (0.99 g, 0.01 mol), methanol (10 mL) and piperidine (5 drops) is heated at reflux for one hour and allowed to cool. The resulting crystalline product is collected by filtration, washed with methanol and dried in air (yield—1.0 g). When dissolved in methylene chloride the product absorbs UV light strongly and has an absorption maximum ($\lambda$max) at 334 nm. Mass spectroscopy analysis supports the following proposed structure:

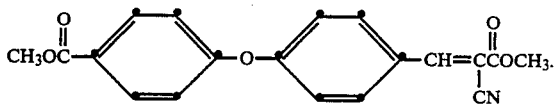

Additional examples of methine compounds which may be used in the preparation of our novel polymer compositions are set forth in the following Table. These compounds may be prepared according to the procedures described above and conform to the formula

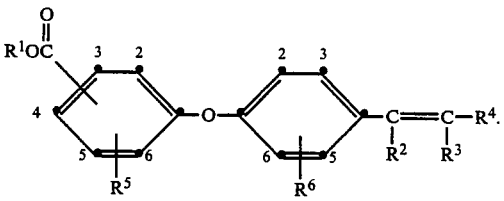

TABLE

| Ex. | —COR$^1$ | R$^5$ | R$^6$ | R$^2$ | R$^3$ | R$^4$ |
|---|---|---|---|---|---|---|
| 2 | 4-COOCH$_3$ | H | H | H | —CN | —SO$_2$CH$_3$ |
| 3 | 4-COOCH$_3$ | H | H | H | —CN | —CONH$_2$ |

TABLE-continued

| Ex. | $-\overset{\overset{O}{\|}}{C}OR^1$ | $R^5$ | $R^6$ | $R^2$ | $R^3$ | $R^4$ |
|---|---|---|---|---|---|---|
| 4 | 4-COOCH₃ | H | H | H | —CN | —CONHCH₂CH₂OH |
| 5 | 4-COOCH₃ | H | H | H | —CN | —CN |
| 6 | 4-COOH | H | H | H | —CN | —SO₂C₆H₅ |
| 7 | 4-COOCH₂CH₂OH | H | H | H | —COOCH₃ | —C=N—1,2-C₆H₄O |
| 8 | 4-COO(CH₂)₃CH₃ | H | H | H | —COOC₂H₅ | —C=N—1,2-C₆H₄S |
| 9 | 4-COOC₆H₅ | H | H | H | —COOC₂H₅ | —COOC₂H₅ |
| 10 | 4-COOCH₂CH₂OCH₃ | H | H | H | —CN | —C₆H₄—4-CN |
| 11 | 4-COOCH₂CH₂Cl | H | H | H | —CN | —C₆H₄—4-COOCH₃ |
| 12 | 4-COOC₆H₅ | H | H | H | —CN | —COC₆H₅ |
| 13 | 4-COOCH₂CH₂C₆H₅ | H | H | H | —CN | —COC(CH₃)₃ |
| 14 | 4-COOCH₂CH₂OC₆H₅ | H | H | H | —COOCH₃ | —COC(CH₃)₃ |
| 15 | 4-COOCH₂C=CHCH=CHO | H | H | H | —CN | —CONHC₆H₅ |
| 16 | 4-COOCH₂CH₂CN | H | H | H | —CN | —CON(C₂H₅)₂ |
| 17 | 4-COOC₆H₄—4-CH₃ | H | H | H | —CN | —CON(CH₃)C₆H₅ |
| 18 | 4-COOCH₂CH=CH₂ | H | H | H | —CN | —CONHC₆H₄—4-OCH₃ |
| 19 | 3-COOCH₃ | H | H | H | —CN | —COOC₂H₅ |
| 20 | 3-COOH | H | H | H | —CN | —COOH |
| 21 | 2-COOCH₃ | H | H | H | —CN | —COOCH₃ |
| 22 | 2-COOC₆H₅ | H | H | H | —CN | —CN |
| 23 | 4-COOCH₂CH₂OOCCH₃ | H | H | H | —CN | —SO₂C₆H₄—4Cl |
| 24 | 4-COOCH₃ | H | H | H | —CN | —SO₂C₆H₄—4-CH₃ |
| 25 | 4-COOC₆H₁₁ | H | H | H | —CN | —C=CHCH=C(COOCH₃)S |
| 26 | 4-COOC₆H₁₀—4-CH₃ | H | H | H | —CN | —C=NN=C(CH₃)S |
| 27 | 4-COOCH₂C₆H₁₀—4CH₂OH | H | H | H | —CN | —C=N—1,2-C₆H₄NH |
| 28 | 4-COOCH(CH₃)₂ | H | H | H | —CN | —C=NN=C(CH₃)O |
| 29 | 4-COO(CH₂)₆OH | H | H | H | —CN | —C=CHNHCH=CH |
| 30 | 4-COOCH₂CH₂NHCOCH₃ | H | H | H | —CN | —C=CHN=CHCH=CH |
| 31 | 4-COOCH₃ | 2-CH₃ | H | H | —CN | —COOCH₃ |
| 32 | 4-COOCH₃ | 2-OCH₃ | H | H | —CN | —COOH |
| 33 | 3-COOCH₃ | 5-COOCH₃ | H | H | —CN | —SO₂(CH₂)₃CH₃ |
| 34 | 2-COOCH₃ | 5-COOCH₃ | H | H | —CN | —CONHC₆H₁₁ |
| 35 | 4-COOCH₃ | H | 3-CH₃ | H | —CN | —CONHCH₂C₆H₅ |
| 36 | 4-COOH | H | 3,5-di-CH₃ | H | —CN | —SO₂C₆H₁₁ |
| 37 | 4-COOCH₃ | H | 2,6-di-OCH₃ | H | —CN | —CN |
| 38 | 4-COOCH₃ | H | 3-Cl | H | —CN | —CONHCH₃ |
| 39 | 3-COOCH₃ | H | 2-Br | H | —CN | —C=N—1,2-C₆H₄NCH₃ |
| 40 | 2-COOCH₃ | 4-CH₃ | 3-CH₃ | H | —CN | —C=CHN(C₂H₅)CH=CH |
| 41 | 4-COOCH₃ | H | 2-OCH₃ | H | —COOCH₃ | —COOCH₃ |
| 42 | 4-COOCH₃ | H | 2-OCH₃ | H | —CN | —COOCH₃ |
| 43 | 4-COOCH₃ | H | 2-OCH₃ | H | —CN | —SO₂C₆H₅ |
| 44 | 4-COOCH₃ | H | H | —CH₃ | —CN | —CN |
| 45 | 4-COOCH₃ | H | H | —C₆H₅ | —CN | —COOCH₃ |
| 46 | 4-COOCH₃ | H | H | —C₆H₁₁ | —CN | —COOC₂H₅ |

TABLE-continued

| Ex. | $-\overset{\overset{O}{\|}}{C}OR^1$ | $R^5$ | $R^6$ | $R^2$ | $R^3$ | $R^4$ |
|---|---|---|---|---|---|---|
| 47 | 4-COOCH$_3$ | H | 2-OCH$_3$ | H | —CN | —C=N—1,2-C$_6$H$_4$—C(O)NCH$_3$ |
| 48 | 4-COOCH$_3$ | H | 2-OCH$_3$ | H | —CN | —C=N—1,2-C$_6$H$_3$—4-CH$_3$—C(O)NH |
| 49 | 4-COOCH$_3$ | H | H | H | —CN | —C=CHCH=C(COOCH$_3$)O |
| 50 | 4-COOCH$_3$ | H | H | H | —COOC$_2$H$_5$ | —SO$_2$C$_6$H$_5$ |
| 51 | 4-COOCH$_3$ | H | H | H | —CN | —C$_6$H$_3$—2,5-di-Cl |
| 52 | 4-COOCH$_3$ | H | H | H | —CN | —CONHC$_6$H$_3$—2,5-di-OCH$_3$ |
| 53 | 4-COOH | H | H | H | —CN | —C=N—1,2-C$_6$H$_4$C(O)NH |
| 54 | 4-COOCH$_3$ | H | 2,6-di-CH$_3$ | H | —CN | —COOCH$_3$ |

EXAMPLE 55

The following materials are placed in a 500-mL, three-necked, round-bottom flask:

97 g (0.5 mol) dimethyl terephthalate
62 g (1.0 mol) ethylene glycol
0.00192 g Ti from a n-butanol solution of acetyltriisopropyl titanate
0.0053 g Mn from an ethylene glycol solution of manganese acetate
0.0345 g antimony trioxide
0.0072 g Co from an ethylene glycol solution of cobaltous acetate The flask is equipped with a nitrogen inlet, stirrer, vacuum outlet, and condensing flask. The flask and contents are heated at 200° C. in a Belmont metal bath for 60 minutes and at 210° C. for 75 minutes with a nitrogen sweep over the reaction mixture. Then 1.57 mL of an ethylene glycol slurry of a mixed phosphorus ester composition (Zonyl A) which contains 0.012 g phosphorus is added. The temperature of the bath is increased to 230° C. At 230° C., methyl 4-[4-(2-methoxycarbonyl-2-cyanovinyl)phenoxy]benzoate (0.0384 g) is added to the flask. Five minutes after this addition, a vacuum with a slow stream of nitrogen bleeding in the system is applied over a five-minute period until the pressure is reduced to 200 mm Hg. The flask and contents are heated at 230° C. under a pressure of 200 mm Hg for 25 minutes. The metal bath temperature is increased to 270° C. At 270° C. the pressure is reduced slowly to 100 mm Hg. The flask and contents are heated at 270° C. under a pressure of 100 mm Hg for 30 minutes. The metal bath temperature is increased to 285° C. and the pressure is reduced slowly to 4.5 mm Hg. The flask and contents are heated at 285° C. under pressure of 4.5 mm Hg for 25 minutes. Then the pressure is reduced to 0.25 mm Hg and polycondensation is continued for 40 minutes. The flask is removed from the metal bath and is allowed to cool in a nitrogen atmosphere while the polymer crystallizes. The resulting polymer has an inherent viscosity of 0.52 measured in a 60/40 ratio by weight of phenol/tetrachloroethane at a concentration of 0.5 g per 100 mL. An amorphous 14 mil thick film molded from this polymer to simulate the sidewall of a container transmits less than 10% light from 355 nm where a 14 mil film prepared from a like polyester without the copolymerized absorber transmits greater than 10% light at all wavelengths above 320 nm.

The inherent viscosities (I.V. of the copolyesters described herein are determined according to ASTM D2857-70 procedure in a Wagner Viscometer of Lab Glass Inc. of Vineland, N.J. having a 1/2 ml capillary bulb, using a polymer concentration of 0.5%, by weight, in 60/40, by weight, phenol/tetrachloroethane solvent. The procedure comprises heating the polymer/solvent system at 120° C. for 15 minutes to enhance dissolution of the polymer, cooling the solution to 25° C. and measuring the time of flow at 25° C. The I.V. is calculated from the equation $$\{\eta\}_{0.50\%}^{25° C.} = \frac{\ln \frac{t_s}{t_o}}{C}$$

where:
$\{\eta\}$ = Inherent viscosity at 25° C. at a polymer concentration of 0.5 g/100 ml. of solvent;
ln = Natural logarithm;
$t_s$ = Sample flow time;
$t_o$ = Solvent-blank flow time; and
C = Concentration of polymer in grams per 100 ml. of solvent = 0.50.

The nonextractabilities of the methine residues described herein are determined as follows:

All extractions are done in glass containers with distilled solvents under the time and temperature conditions described below. The sample form is ½ inch×2½ inch segments cut from the cylindrical side wall portion of 2-liter bottles. All samples are washed with cold solvent to remove surface contaminants and are exposed using 200 ml solvent/100 in.² surface area (2 ml/in.²).

Solvent blanks are run under the same extraction conditions without polymer. In most cases samples were extracted, spiked, with a known amount of additive as a control, and analyzed in duplicates. The solvents employed and the extraction conditions for each solvent are:

1. Water. The samples at room temperature are added to solvent and heated to 250° F. for two hours. Half of the samples are then analyzed and the remainder are placed in a 120° F. oven for 30 days.

2. 50% Ethanol/Water. The samples at room temperature are added to the solvent at room temperature, placed in an oven at 120° F. and analyzed after 24 hours and 30 days.

3. Heptane. The samples at room temperature are added to solvent at room temperature and heated at 150° F. for two hours. Part of the samples are cooled to room temperature and analyzed spectrophotometrically and the remainder are allowed to age at 120° F. for 30 days before analysis.

Any suitable analytical technique and apparatus may be employed to determine the amount of methine residue extracted from the polymer.

The invention has been described in detail with particular reference to preferred embodiments thereof, but it will be understood that variations and modifications can be effected within the spirit and scope of the invention.

We claim:

1. A composition comprising molding grade condensation polymer having copolymerized therein a total of about 100 to 800 parts by weight per million parts by weight polymer of the residue of a methine compound or mixture of methine compounds having the formula

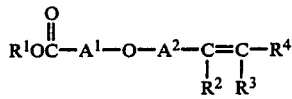

wherein
$R^1$ is hydrogen or an unsubstituted or substituted alkyl, alkenyl, cycloalkyl or aryl radical;
$A^1$ is an unsubstituted or substituted phenylene radical;
$A^2$ is an unsubstituted or substituted 1,4-phenylene radical;
$R^2$ is hydrogen or an unsubstituted or substituted alkyl, cycloalkyl or aryl radical;
$R^3$ is cyano or

and
$R^4$ is one of the substituents which $R^3$ can represent or an unsubstituted or substituted carbamoyl, alkanoyl, aroyl, alkylsulfonyl, arylsulfonyl, aryl or aromatic heterocyclic radicals.

2. The composition of claim 1 wherein the polymer is a linear polyester and the methine compound has the formula

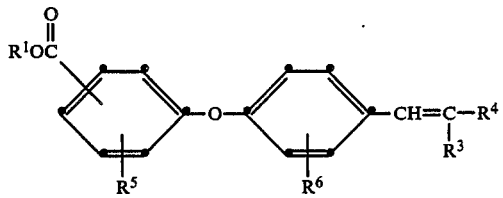

wherein
$R^1$ is hydrogen or alkyl;
$R^3$ is cyano or

$R^4$ is one of the substituents which $R^3$ can represent or carbamoyl, alkanoyl, alkylsulfonyl, arylsulfonyl, phenyl or tolyl; and $R^5$ and $R^6$ each independently is hydrogen, alkyl, alkoxy, halogen or

3. A composition of claim 1 wherein the polymer is a linear polyester and the methine compound has the formula

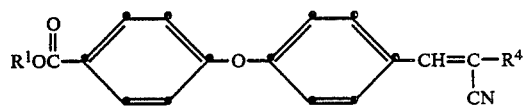

wherein
$R^1$ is hydrogen or lower alkyl; and
$R^4$ is cyano, lower alkoxycarbonyl, carbamoyl, lower alkylsulfonyl, phenylsulfonyl, tolylsulfonyl, phenyl or tolyl.

4. The composition of any of claims 1 to 3 wherein the polyester acid moiety is comprised of at least about 50 mol % terephthalic acid residue, and the glycol moiety at least about 50 mol % ethylene glycol or 1,4-cyclohexanedimethanol residue.

5. The composition of any of claims 1 to 3 wherein the polyester is comprised of from about 75 to 100 mol % terephthalic acid residue and from about 75 to 100 mol % ethylene glycol residue.

6. The composition of claim 1 wherein the polymer is unsaturated polyester having an acid moiety comprised of fumaric or maleic acid or mixtures thereof and up to about 60 mol % of one or a mixture of o-phthalic, isophthalic, or terephthalic acids, and having a glycol moiety comprised of one or a mixture of propylene glycol, neopentyl gylcol, 2,2,4-trimethyl-1,3-pentanediol, ethylene glycol or diethylene glycol.

7. The composition of claim 6 wherein the acid moiety is comprised of from about 75 to 100 mol % o-phthalic acid and maleic acid in a mole ratio of from about 1/2 to about 2/1, and the glycol moiety is comprised of from about 75 to 100 mol % propylene glycol.

8. The composition of claim 6 containing a curing amount of an ethylenically unsaturated monomer.

9. A cured, formed article of the composition of claim 8.

10. A fiber of the conposition of claim 1 dyed with from about 0.01 to about 5.0% by weight based on weight of fiber of a disperse dye.

11. A formed article of the composition of claim 1.
12. A formed article of the composition of claim 4.
13. A formed article of the composition of claim 5.
14. A formed article of the composition of claim 6.